United States Patent [19]

Kosanke et al.

[11] Patent Number: 5,695,541
[45] Date of Patent: Dec. 9, 1997

[54] PROCESS FOR PREPARATION OF BACTERIAL AGRICULTURAL PRODUCTS

[75] Inventors: John W. Kosanke, Waukesha; Robert M. Osburn, Shorewood; Raymond S. Smith, Whitefish Bay, all of Wis.

[73] Assignee: LiphaTech, Inc., Milwaukee, Wis.

[21] Appl. No.: 612,395

[22] Filed: Nov. 13, 1990

[51] Int. Cl.$^6$ ..................................................... C05F 11/08
[52] U.S. Cl. ................................................ 71/7; 47/57.6
[58] Field of Search ............................. 71/6, 7; 47/57.6

[56] References Cited

U.S. PATENT DOCUMENTS

| | | | |
|---|---|---|---|
| 2,932,128 | 4/1960 | Porter et al. | 71/6 X |
| 3,115,404 | 12/1963 | Carney | 71/6 |
| 3,168,796 | 2/1965 | Scott et al. | 71/7 X |
| 3,898,132 | 8/1975 | Hettrick | 71/6 X |
| 4,875,921 | 10/1989 | Penn | 71/7 |
| 4,878,936 | 11/1989 | Handlesman et al. | 71/7 |

FOREIGN PATENT DOCUMENTS

| | | |
|---|---|---|
| 0203708 A1 | 3/1986 | European Pat. Off. . |
| 0192342 A2 | 8/1986 | European Pat. Off. . |
| 0223662 A1 | 5/1987 | European Pat. Off. . |
| 0226394 A2 | 6/1987 | European Pat. Off. . |
| 0286351 A2 | 12/1988 | European Pat. Off. . |
| 0314439 A2 | 3/1989 | European Pat. Off. . |
| 8702660 | 5/1987 | WIPO ............................. 71/6 |

OTHER PUBLICATIONS

Stotzky, Interactions of Soil Minerals with Natural Organics and Microbes, Ch. 10, po. 305–427 (1986), no month.
Madkour et al., Applied & Environmental Microbiology 56 (9): 2876–2881, no date.
LeRudulier et al., Science 224:1064–1068, no date.
Csonka, Microbiol. Rev., vol. 53, No. 1, p. 121–147 (1989), no month.
LeRudulier et al., FEMS Microbiol. Reviews, 39, 67–72, no date.
Pocard et al., Plant Physiol. Biochem. 26(2): 224, no date.
Smith et al. 1988, J. Bact. 170 (7): 3142–3149, no month.
Fougere et al., 1990, J. Gen. Microbiol. 136: 157–163, no month.
Crowe et al., 1989, Science 223: 701–703, no month.
Galinski et al., 1990 Archives of Microbiology 153: 607–613, no month.
McBride et al., 1989, J. Bact. 171(11): 6383–6386, no month.
Smith et al., 1989, J. Bact. 171(9): 4714–4717, no month.
Suslow, "Role of Root Colonizing Bacteria in Plant Growth", Phytopathogenic Prokaryotes, vol. 1, Mount and Lacy Eds. 1982, no month.
Lifshitz et al., Phytopathology Reviews in Biotechnology, vol. 7, Issue 2, 1988, pp. 97–106, no month.
Mary et al., App. Environ. Microbiol. 1985, vol. 50, No. 2, pp. 207–211, no month.
Anyheunisse et al., Antonie va Leeuwenhoek 45 (1979) 177–184, no month.
Sleesman et al., Ecology and Epidemiology, 1976, vol. 66, No. 11, pp. 1334–1338, no month.
Hume, Agronomy Abstracts, 1990 Annual Meeting, Oct. 21–26, p. 145, no month.

*Primary Examiner*—Ferris Lander
*Attorney, Agent, or Firm*—Foley & Lardner

[57] ABSTRACT

A process for producing a dried bacterial agricultural product having superior viability initially involves culturing (fermenting) a species of microorganism in a growth medium to form a culture. The culture containing the microorganism plus the growth medium is then mixed with a carrier. The resulting mixture is incubated for at least one day to increase the microorganism count in the mixture. The mixture is then air dried slowly for at least about one day so the moisture level in the microorganisms is gradually reduced to form the dried composition. The process may further include steps of milling and then coating seeds with the composition. An inoculant composition according to the invention, which may be made by the foregoing process, consists essentially of a clay carrier and at least $10^9$ viable bacteria per gram of the composition. Compositions containing biocidal microbes which combat insects, fungi or the like, and other useful microbes, such as growth promoting bacteria, may also be prepared.

10 Claims, No Drawings

PROCESS FOR PREPARATION OF BACTERIAL AGRICULTURAL PRODUCTS

TECHNICAL FIELD

This invention relates to an improved slow drying process for bacterial agricultural inoculants and other compositions which results in increased bacterial viability.

BACKGROUND OF THE INVENTION

Leguminous plants fix nitrogen from the air and convert it to organic nitrogenous compounds used by the plant for protein synthesis. Nitrogen fixation in leguminous plants is possible because of the symbiotic relationship with bacteria of the genera Rhizobium and Bradyrhizobium, which form nodules on the roots of legumes. Different species cause nodulation in specific legume species. Maximum symbiotic nitrogen fixation occurs when plant and bacteria are properly matched, and when nodule formation is maximized. *B. japonicum* is associated with soybean, *R. leguminosarum* biovar trifolii with clovers, *R. meliloti* with alfalfa and sweetclovers, *R. leguminosarum* biovar viceae with peas and vetches, *R. leguminosarum* biovar phaseoli with garden variety beans, and *B. lupini* with lupines.

It is common practice to inoculate leguminous plants with rhizobia to aid nodule formation. Inoculation can be accomplished by coating seeds, dusting on-farm of seeds or crops, or placing inoculant in-furrow at planting time. Previous methods of producing an inoculant have included mixing an active, living rhizobia bacterial culture with a carrier such as humus or peat. The moist carrier maintains the bacteria in a living state. However, the shelf life of such a live bacterial culture is short due to depletion of food and moisture in the environment.

Another method of preparing inoculants is by converting bacteria to a dormant state. U.S. Pat. No. 3,168,796 to Scott, et al describes a method of preparing an inoculant including a step of freeze-drying bacteria to a dormant state at temperatures of $-35°$ to $-70°$ C. This process must be done rapidly to prevent cell rupture. The dried, ground bacteria are mixed with a powdered carrier such as kaolin or montmorillonite. Freeze-drying gives a poor initial recovery of bacteria, although the inoculant remains stable for long storage periods.

Another method of preparing a dry, dormant inoculant is cited in U.S. Pat. No. 4,875,921 to Agracetus Corp. To make the inoculant, a suspension of bacteria is maintained, then separated from its culture medium. Concentrated cells are kept for 0–96 hours under aseptic conditions. The culture is mixed with a granular carrier such as vermiculite, perlite, or charcoal. This mixture is air-dried at 22°–30° C. for 2–10 days, again under aseptic conditions. The culture to carrier ratio is in the range of 0.5–1.5 by weight. This drying technique is uneconomical insofar as it involves a number of separation and purification steps.

A slow-drying process used by Liphatech, Inc. prior to the present invention in the production of rhizobial inoculants involved successive steps of fermenting the rhizobia, mixing in powdered peat as the carrier together with calcium carbonate to neutralize the peat, air-drying for a week in the presence of a dehumidifier to a water content of 20–22 wt. %, and then milling, which further reduced the moisture content to 12 wt. %. This process proved useful but produced a inoculant with less than optimum bacterial viability and seed adhesion.

Another currently available product sold under the tradename "Dormal" by Research Seeds utilizes a clay mixture of montmorillonite and kaolinite as the carrier, but has bacteria levels of only $10^8$ or less as measured by the slow rehydration method described in Example 6 below. Research has suggested that rates of drying, temperature, relative humidity and culture age affect the survival of bacteria such as rhizobia, *E. coli*, and other species. See Mary et al., *App. Environ. Microbiol.* 1985 Vol. 50, No. 2, pp. 207–211, Anyheunisse et al., *Antonie van Leeuwenhoek* 45(1979) 177–184, and Sleesman et al., *Ecology and Epidemiology* 1976 Vol. 66, No. 11, 1334–1338. The effects of clay minerals have also been studied; see Stotzky, *Interactions of Soil Minerals with Natural Organics and Microbes*, Chapter 10, pp. 305–427 (1986). However, a need remains for a process for making a dry bacterial inoculant composition having greater viability and shelf life, and for a more economical, efficient process for producing such a composition.

Recent studies have established that bacteria can produce substances known as osmoprotectants to counter the effects of osmotic stress. See Madkour et al., *Applied & Environmental Microbiology* 56 (9): 2876–2881, and LeRudulier et al. *Science* 224:1064–1068. A wide variety of osmoprotectants have been studied. See Csonka, *Microbiol. Rev.*, Vol. 53, No. 1, p. 121–147 (1989), the contents of which are incorporated by reference herein. Betaine is an osmoprotectant synthesized by organisms such as Rhizobium, *Ectothiorhodospira halochloris*, *Klebsiella pneumoniae*, and *Escherichia coli*, among others. See LeRudulier et al. *FEMS Microbiol. Reviews* 39: 67–72, Pocard et al. *Plant Physiol. Biochem.* 26(2): 224, Smith et al. 1988 *J. Bact.* 170(7):3142–3149, and Fougere et al. 1990 *J. Gen. Microbiol.* 136:157–163. Trehalose is another known osmoprotectant, as discussed in Crowe et al. 1989 *Science* 223:701–703, Galinski et al., 1990 *Archives of Microbiology* 153:607–613, and McBride et al. 1989 *J. Bact.* 171(11): 6383–6386. A dipeptide has also been identified as an osmoprotectant in *R. meliloti*. Smith et al., 1989 *J. Bact.* 171(9):4714–4717. Rapid drying techniques do not allow these osmoprotectant capabilities to evolve. As discussed below, slow drying techniques can be altered to provide optimum conditions for the appearance of osmoprotectants, thus increasing survival of bacteria upon dehydration.

Interest in dry, dormant bacterial products has increased due to recent interest in biological pesticides as an ecological alternative to conventional chemical particles. For example, Pseudomonas bacteria are known to have antifungal and growth promoting properties for a variety of plates, particularly agronomically important crops; see Suslow, "Role of Root Colonizing Bacteria in Plant Growth", *Phytopathogenic Prokaryotes*, Vol. 1, Mount and Lacy Eds. 1982. A strain of *Bacillus cereus* is known to enhance nodulation of soybean, as described in Handlesman et al. U.S. Pat. No. 4,878,936, issued Nov. 7, 1989. Fungi such as Trichoderma have growth promoting effects on the nodulation of soybeans and antifungal effects. See Lifshitz et al., *Phytopathology* Vol. 76, No. 7, pp. 720–725 (1986), Baker, *CRC Critical Reviews in Biotechnology*, Vol. 7, Issue 2, 1988, pp. 97–106, and Hume, *Agronomy Abstracts*, 1990 Annual Meeting October 21–26, p. 145. The present invention addresses this need for a biological pesticide composition that retains viability until application to the target crops.

SUMMARY OF THE INVENTION

This invention provides a process for producing a dried bacterial agricultural product having superior viability. The process initially involves culturing (fermenting) a species of microorganism in a growth medium to form a culture. The culture containing the microorganism plus the growth medium is then mixed with a carrier. The resulting mixture is incubated for at least one day to increase the microorganism count in the mixture. The mixture is then air dried slowly for at least about one day so the moisture level in the microorganisms is gradually reduced to form the dried composition. The process may further include steps of milling and then coating seeds with the composition.

An inoculant composition according to the invention, which may be made by the foregoing process, consists essentially of a clay carrier and at least $10^9$ viable bacteria per gram of the composition. Compositions containing biocidal microorganisms which combat insects, fungi or the like, or other useful microorganisms, such as microorganisms which have growth promoting effects other than symbiotic nitrogen fixation, may also be prepared according to the invention.

According to a further aspect of the invention, an osmoprotectant such as betaine is added to the composition to increase survival of the microorganism in dried culture. Other objects, features and advantages of the present invention will become apparent from the following detailed description. It should be understood, however, that the detailed description and specific examples are given by way of illustration only, since various changes and modifications within the spirit and scope of the invention will be apparent to those skilled in the art.

DETAILED DESCRIPTION

One aspect of the invention provides an improved slow-drying process for producing a dried bacterial agricultural product useful as an inoculant or biocide, and which results in increased bacterial survival for longer storage periods and upon revitalization. A preferred process according to the invention involves culturing a species of inoculant bacteria in a growth medium within a conventional fermentor to form a culture. The culture containing the bacteria plus the growth medium is then mixed with an inert powdered or granular clay carrier. The resulting mixture is incubated for 1–7 days at room temperature with no dehumidification to increase bacteria count in the mixture. The mixture is then air dried slowly, e.g., for about 1–14 days under non-aseptic conditions, so that the moisture level in the mixture is gradually reduced to less than 15% to form the inoculant composition. The resulting clay aggregates may then be milled to a powder form. These steps and the materials used therein are described in detail hereafter.

The carrier in this embodiment of the invention comprises clay, preferably a mixture of montmorillonite and kaolinite which has an essentially neutral pH. Clay provides superior properties upon drying as compared to peat, charcoal and other commonly used carriers when used with rhizobia. A preferred carrier is a blend of nonsterile kaolinite and montmorillonite in a weight ratio ranging from 1:2 to 4:1 kaolinite to montmorillonite, most preferably about 2:1. Kaolinite is a acidic clay, while montmorillonite is basic. The foregoing ratios give the final carrier a generally neutral pH, i.e. from 5 to 8, preferably about 7.9. This mix of clays provides a neutral or slightly basic environment which is advantageous for bacterial survival when moisture is subsequently encountered at planting. Kaolinite causes better adherence to seed coats. Montmorillonite is nontoxic and will not inhibit growth at revitalization. The amphoteric quality of this carrier also may enhance clinging of the bacteria to the carrier. The nonhygroscopic nature of these clays is also advantageous to the slow-drying process.

An organic amendment such as soybean flour, wheat bran, cottonseed flour or similar nutrients may be added to the carrier to provide a food source during incubation. The amount of the organic amendment is generally in the range of from about 1 to 25 wt. % based on the carrier for optimum growth. See Examples 3, 6 and 8 below. Surprisingly, use of more than 25 wt. % flour actually decreased the bacteria count following incubation.

The carrier may be in powdered or granular form depending on intended use. Final particle sizes of from about 0.1 to 150 microns have been found to yield the foregoing advantages most effectively. Powders are used for coating seeds, whereas granules are used for in-furrow application. Granules according to the invention may be made using commercially available pregranulated clay, such as Oran Creek-O-Nite® 20/50 LVM (20/50 mesh size). A nutrient may be preblended with the granules as described above.

The bacteria for use in an inoculant composition according to the invention is one of the genera Rhizobium or Bradyrhizobium which nodulates one or more host plant species. Preferred bacteria include B. japonicum, R. meliloti, R. leguminosarum biovar trifolii, viceae and phaseoli, Bradyrhizobium species for peanut, and B. lupini, but are not limited to these.

Bacteria of the selected species are first cultured in a suitable nutrient medium, such as a yeast extract-sucrose broth for R. meliloti, for a period such as about 1 to 4 days at a temperature in the range of about 26° to 30° C. to achieve a final concentration of at least $10^9$ colony forming units (cfu's) per ml. A variety of culture media for known bacterial species are well known in the art. The culture containing the bacteria plus the growth medium is then mixed with the inert powdered or granular clay carrier. The culture to clay carrier ratio in the mixing step is less than about 1:2, preferably in the range of 1:2 to 1:4, and most preferably about 1:3 to 1:4 to provide the best consistency.

It is important that the bacteria are not separated from the growth medium at this stage, since the resulting mixture is then incubated for at least 1 day, preferably 1–7 days at room or slightly elevated temperature (20°–30° C.), preferably with no dehumidification. This incubation step in the presence of the carrier increases the bacterial count before drying. Conditions are adjusted so that the mixture at this stage has a moisture level in the range of 25 to 33 wt. %, particularly 26–27% for powdered clay and 30–31% for granular clay. Incubation increases bacterial survival by increasing the number of bacteria as well as stabilizing the culture.

The incubated mixture is then slowly air-dried for a period of at least about 24 hours, preferably from 1–14 days. For rhizobia, a period of 3–14 days is preferred. Forced-air drying may be used, but simply room-air drying in trays or similar containers is most effective. An advantage of the invention is that this and the other steps of the process may be carried out under non-aseptic conditions. Drying is preferably conducted at a temperature of about 20°–30° C., typically 21°–24° C., and a relative humidity of less than 75%, preferably about 35–60%. The moisture level is gradually reduced to less than 15 wt. % as discussed below.

Drying at a relative humidity less than 75% optimizes bacterial survival during desiccation. At a temperature range of 20°–30° C., drying occurs at a rate which allows sufficient time for the production of osmoprotectants by the bacteria, facilitating increased survival. Osmoprotectants are small organic molecules such as betaine, trehalose, proline, choline, glutamate, glutamine, and γ-amino-butyrate that prevent damage from cellular dehydration by balancing the osmotic strength of the cytoplasm with that of the environment. It has been found according to the present invention that these compounds can also provide desiccation tolerance. Betaine can also function in *R. meliloti* as a carbon, nitrogen, and energy source, as well as an osmoprotectant. In a nitrogen and carbon-free medium, *R. meliloti* can use betaine for growth, i.e., betaine acts as a nutrient.

According to a further aspect of the invention, an osmoprotectant and/or bacterial nutrient such as betaine or trehalose is added directly to the culture or to the culture-carrier mixture, preferably in liquid or powder form, during the fermentation step before mixing the culture with the carrier, in order to further enhance survival of the bacteria. The amount added should be sufficient to improve the osmotic properties of the cells. For betaine, a concentration of from about 0.5 to 10 micromoles (mmol) in the culture may be used.

The final moisture level is less than about 15 wt. %, i.e., is low enough to render the bacteria dormant. For clay powders, the maximum is preferably about 10 wt. %. A range of 1 to 5 wt. % moisture is preferred. These and other moisture levels described herein are on a wet weight basis. Alternatively, water activity (Aw) indicates the relative availability of water to the bacteria in the mixture. Water activities less than 0.95, preferably about 0.4 to 0.6, have proven most suitable for both powders and granules. Low moisture levels provide greater longevity.

The dried product is then milled using an air classifier mill to a final particle size of 0.1 to 150 microns. This range is optimum for adherence purposes, making the seed inoculation process more efficient. The product may then be packaged and stored for later use, or used immediately for coating seeds. In either case, suitable conditions for survival in storage are 1° to 30° C., particularly about 1° to 10° C. Coated seeds made using the composition of the invention can be stored and shipped, and remain effective for periods of 18 months or longer. Compositions according to the invention may also be used in dry powder form to preinoculate legume seeds with rhizobia, or for on-farm application of biological disease control agents (BDC) or plant growth promoting rhizobacteria (PGPR). In granular form the compositions of the invention may be used for in-furrow application of inoculant.

The process of the invention provides a superior inoculant composition which consists essentially of bacteria of the genus Rhizobium with residual culture medium in a clay carrier. The count of viable bacteria in such a carrier upon rehydration, particularly by the slow rehydration procedure set forth below, exceeds about $10^9$ bacteria per gram of the composition, and generally ranges from about $1.1\times10^9$ to $1.1\times10^{10}$ bacteria per gram. The water level of the composition is preferably less than about 5 wt. %, especially 1% to 4%. The composition further contains nutrients from the original culture which can serve as a growth media for the bacteria upon rehydration. As noted above, the culture:carrier weight ratio prior to drying is about 1:2 to 1:4. An inoculant composition having the foregoing characteristics has a shelf life of 18 months or more.

According to a further aspect of the invention, the process of the invention may be used with any kind of bacteria or other microorganism capable of surviving in a desiccated state. Of particular interest are bacteria which have biocidal properties, such as pesticidal and other properties, and growth promoting bacteria (PGPR's) which are capable of living in the soil in the presence of the plant to be protected. A number of bacteria of this kind are known, including *Pseudomonas putida* having activity against Pythium useful in protecting dry bean and other crops and having plant growth promotion capability, and *Bacillus cereus*, which acts as an anti-fungal agent and growth promoter for agronomically important plants such as soybeans, corn, and the like. Other known biocidal microorganisms include fungi such as trichoderma and gliocladium, bacteria such as serratia and erwinia, and actinomycetes including streptomyces and nocardia. All of the foregoing microorganisms can be used in the process of the invention to make biocidal compositions comprising the biocidal microbe in a dried, dormant state and the particulate or granular carrier.

According to this embodiment of the invention the optimum carrier may vary depending on the specific species of bacteria employed. The foregoing clay carrier may be used, as well as other known carriers such as peat, alginate beads, charcoal, vermiculite, and perlite. However, as demonstrated by the examples below, a clay-based carrier is preferred.

This invention solves problems inherent in previous slow-drying techniques by providing conditions which increase bacterial survival during the desiccation process and provide a better environment for bacteria upon rehydration at planting. The process of the invention has wide applicability to species of bacteria other than rhizobia, and is also simpler and less expensive compared to previous methods, since it does not require stringent conditions and omits separation and purification steps. The dried bacterial composition of the invention remains effective for longer storage periods than previous products, and provides a higher count of viable bacteria upon rehydration.

The following examples illustrate the invention.

EXAMPLE 1

A strain of *Rhizobium meliloti* selected for its ability to survive desiccation was grown in yeast extract-sucrose broth medium for 67 hours and achieved a population of $2.6\times10^9$ cfu/ml. FD & C Yellow #5 dye was then added to the culture (0.5% w/v) prior to mixing-in the carrier. The carrier was comprised of nonsterile pre-blended kaolinite and montmorillonite clays (2:1 w/w). Formulation was achieved by slowly mixing one part culture/dye mixture to three parts carrier.

This formulation had a moisture level of 27%, or a water activity of greater than 0.99. Solid-phase fermentation (incubation) continued for four days at room temperature (21° C.), followed by drying over the period of 11 days at 21°–24° C. and 35–60% relative humidity resulting in a final moisture of 4.6%. This dry material was milled to obtain a particle size of 0.1–150 microns to ensure good adherence to seed. This final dry, stable microbial product had a moisture of 4.0% (Aw=0.497) and a viable cell count of $1.3\times10^9$ rhizobia/gram.

Table 1 shows the survival of the rhizobia in the carrier over time as determined by plate count assays. Viability of the bacteria on seed was also determined by coating the dry Rhizobium product onto Vernal alfalfa seed in an amount of 3.78 g/lb. of seed (Table 2).

TABLE 1

| Dry Clay product | Initial cfu/g | 10-month cfu/g |
|---|---|---|
| 24° C. Storage | $1.3 \times 10^9$ | $9.3 \times 10^8$ |
| 7° C. Storage | $1.3 \times 10^9$ | $1.1 \times 10^9$ |

TABLE 2

| Coated Seed | Initial cfu/seed | 6-month cfu/seed |
|---|---|---|
| 24° C. Storage | 6,818 | 2,955 |
| 7° C. Storage | 6,818 | 3,409 |

EXAMPLE 2

The bacterium used in this example was the same strain of Rhizobium meliloti as that in Example 1. This bacterium was grown in yeast extract-sucrose broth medium for six days, after which the culture was used to formulate a product in the same manner as Example 1, except that no FD & C Yellow #5 dye was added prior to mixing-in the carrier. Solid-phase fermentation continued for seven days followed by drying over the period of 11 days (as in Example 1) to achieve a final moisture of 3.9%. Following milling of the dry materials to a particle size equivalent to that of Example 1, the sample was assayed for viable cell count (Table 3).

TABLE 3

| | Initial (cfu's/g) | 3 months (cfu's/g) |
|---|---|---|
| Formulation without dye | $1.8 \times 10^9$/g | $1.1 \times 10^9$/g |

EXAMPLE 3

The bacterium used in this example was the same strain of Rhizobium meliloti as that in Examples 1 and 2. This bacterium was grown in yeast extract-sucrose medium for 72 hours, after which the culture was mixed with a carrier in the same manner as Example 2. The carrier was the same ratio of pre-blended nonsterile kaolinite and montmorillonite clays plus the addition of (10% w/w) soybean flour. Solid-phase fermentation continued for four days at 21° C. followed by drying over a period of 10 days as in Example 1. The final moisture of the dry clay product was 2.8%. After being ground to a fine powder the dry, stable microbial product was assayed for viable cell count (Table 4).

TABLE 4

| | cfu's/g | | |
|---|---|---|---|
| | Initial | 6 weeks | 3 months |
| Formulation with Soybean Flour | $7.3 \times 10^9$ | $4.6 \times 10^9$ | $2.8 \times 10^9$ |

EXAMPLE 4

The bacterium used in this example was a strain of Rhizobium leguminosarum biovar trifolii. This bacterium was grown in yeast extract-mannitol broth medium for 72 hours and achieved a population of $3.6 \times 10^9$ cfu/ml. This culture was mixed in the same manner as Example 2. Solid-phase fermentation continued for 72 hours, at which point the formulation was divided into two fractions. Both fractions were dried as in Example 1, except that fraction A required only four days of drying because of increased air movement over the carrier, while fraction B required 11 days as in Examples 1 and 2. The final moisture of fraction A was 3.5% while fraction B was 4.5%. After being ground to a fine powder, both fractions were assayed for viable cell count (Table 5).

TABLE 5

| Fraction A - 4 days drying | $1.6 \times 10^9$ cfu/g |
|---|---|
| Fraction B - 11 days drying | $1.5 \times 10^9$ cfu/g |

EXAMPLE 5

The bacterium used in this example was a strain of Pseudomonas putida selected from the rhizosphere of dry bean for its activity against Pythium and its plant growth promotion capability. The bacterium was fermented in broth of King's medium B for 48 hours at 28° C. The culture was added directly to solid matrix carrier at a rate of 3:1 carrier culture resulting in a formulation moisture content of approximately 27% wet weight (0.99 Aw). The solid matrix carrier was composed of a blend of nonsterile kaolinite and montmorillonite clay powders (2:1 w/w) and had a pH of 7.9. The formulation was mixed to a uniform consistency, then solid phase fermented at 22° C. and 50% RH for three days under conditions whereby moisture level was maintained, but the formulation was allowed to aerate with restricted air movement. Upon completion of solid phase fermentation, the formulation was allowed to slowly dry under the same temperature and humidity conditions described above for a period of 12 days to a moisture level of 4.1% (0.54 Aw). The formulation was then mill-ground to a particle size range of 0.1–150 μm. The population density of the resultant dry, stable clay powder formulation at the time of production and after six months is presented in Table 6.

EXAMPLE 6

The bacterium used in this Example was the same as that used in Example 5. It was fermented in broth of King's medium B for 48 hours at 28° C. The culture was added directly to solid matrix carrier at a rate of 3:1 carrier/culture resulting in a formulation moisture content of approximately 27% wet weight (0.99 Aw). The solid matrix carrier was composed of a blend of nonsterile kaolinite and montmorillonite clay powders (2:1 w/w) plus soybean flour (9:1 w/w, clay/soybean flour) and had a pH of 7.2. The formulation was mixed to a uniform consistency, then solid phase fermented at 22° C. and 50% RH for three days under conditions whereby moisture level was maintained, but the formulation was allowed to aerate. Upon completion of solid phase fermentation, the formulation was allowed to slowly dry under the same temperature and humidity conditions described above for a period of 12 days to a moisture of 4.1% (0.54 Aw). The formulation was then mill-ground to a particle size range of 0.1–150 μm. The population density of the resultant dry, stable clay powder formulation at the time of production and after six months is presented in Table 6.

A slow rehydration procedure was used in Examples 1 through 6 to determine the count of viable bacteria in the foregoing compositions according to the invention. In Examples 7 and 8, no special slow rehydration procedures were used, i.e., the microorganisms were rehydrated rapidly by addition of water. References to "slow rehydration" should be understood to mean rehydration by the following procedure or an essentially equivalent procedure.

To carry out slow rehydration, a sample (24 g) of the dried composition is weighed out into a small beaker. Water (8 ml) is added dropwise with manual stirring. The rehydrated sample is allowed to stand at room temperature and humidity for 10 minutes. Water (130 ml) is poured into a small blender, which is then turned on at low speed. A sample (20 g) of the rehydrated composition is then sprinkled into the blender and mixed for 1.5 minutes. The resulting mixture is then removed in predetermined volumes to perform serial dilutions using an initial dilution of $10^{-1}$ rhizobia per gram of the original dry sample. Plate counts are then made by counting colonies formed to determine the number of colony forming units. The cfu count corresponds to the number of viable organisms originally present.

EXAMPLE 7

The bacterium used in this example was the same as that used in Examples 5 and 6. It was fermented in broth of King's medium B for 48 hours at 28° C. The culture was added directly to solid matrix carrier at such a rate as to yield a formulation moisture content of 30.5% wet weight and Aw of 0.99 (approximately 2.3:1 w/w/, carrier/culture). The solid matrix carrier was a nonsterile 20/50 mesh granular clay compound of a mixture of montmorillonite, kaolinite, illite, and quartz amended with soybean flour (9:1 w/w, clay/soybean flour) and calcium carbonate as a neutralizing agent (20:1 w/w/, clay, calcium carbonate) and had a pH of 6.8. The formulation was mixed to a uniform consistency, then solid phase fermented at 22° C. and 50% RH for three days under conditions whereby moisture level was maintained, but the formulation was allowed to aerate. Upon completion of solid phase fermentation, the formulation was allowed to slowly dry under the same temperature and humidity conditions described above for a period of 12 days to a moisture level of 3.6% (0.62 Aw). The population density of the resultant dry, stable clay granule formulation at the time of production and after six months is presented in Table 6.

EXAMPLE 8

The bacterium used in this example was the same as that used in Examples 5, 6, and 7. It was fermented in broth of King's medium B for 48 hours at 28° C. The culture was added directly to solid matrix carrier at such a rate as to yield a formulation moisture content of 30.5% wet weight and Aw of >0.99 (approximately 2.3:1 w/w, carrier/culture). The solid matrix carrier was a nonsterile 20/50 mesh granular clay compound of a mixture of montmorillonite, kaolinite, illite, and quartz amended with soybean flour (9:1 w/w, clay/soybean flour) and had a pH of 5.4. The formulation was mixed to a uniform consistency, then solid phase fermented at 22° C. and 50% RH for three days under conditions whereby moisture level was maintained, but the formulation was allowed to aerate. Upon completion of solid phase fermentation, the formulation was allowed to slowly dry under the same temperature and humidity conditions described above for a period of 12 days to a moisture level of 3.6% (0.62 Aw). The population density of the resultant dry, stable clay granule formulation at the time of production and after six months is presented in Table 6.

TABLE 6

| Example | Formulation population density (cfu/g) Time after initial production (months) | |
|---|---|---|
| | 0 | 6 |
| 5 | $3.9 \times 10^9$ | $2.4 \times 10^9$ |
| 6 | $7.4 \times 10^9$ | $5.1 \times 10^9$ |
| 7 | $9.1 \times 10^9$ | $2.7 \times 10^9$ |
| 8 | $1.1 \times 10^{10}$ | $4.8 \times 10^9$ |

EXAMPLE 9

An *R. meliloti* culture ($3.3 \times 10^9$/ml) was dried in plastic dilution bottles, 1.0 ml per sample. Addition of betaine directly to the cultures to provide a 0.1 mmolar culture concentration and/or NaCl to provide a 0.5 molar culture concentration produced the plate counts given in Table 7, determined after drying. For Sample 3, NaCl was added, and then the sample was air-dried immediately. Samples 1, 2, 4 and 5 were allowed to incubate one hour before being transferred to the drying bottles.

TABLE 7

| Sample | Count |
|---|---|
| 1 - Control | $3.6 \times 10^8$ |
| 2 - Culture + Betaine | $6.6 \times 10^8$ |
| 3 - NaCl (dried immediately) | $5.1 \times 10^5$ |
| 4 - NaCl | $6.1 \times 10^6$ |
| 5 - NaCl + Betaine | $1.2 \times 10^8$ |

In comparing Samples 1 and 2 and also Samples 4 and 5, betaine does improve survival of *R. meliloti* upon desiccation.

EXAMPLE 10

Since betaine addition increased survival of rhizobia in dried culture (see Example 9), its effect in dry clay carrier was then evaluated. This experiment evaluated betaine addition both at mixing and during drying. Samples 1-4 received betaine at mixing, while Samples 5-8 did not. Samples 1 and 8 were incubated for 7 days and then slow-dried in accordance with the invention. Samples 2 and 5 were partially slow-dried to 0.98 Aw, then betaine was added, and then drying was completed. Samples 3 and 6 were treated similarly to Samples 2 and 5, except that an equivalent amount of water was added instead of a betaine solution. Samples 4 and 7 were treated similarly to Samples 2 and 5, except that nothing was added after partial slow-drying.

The initial counts from the experiments are as given in Table 8. The increase in initial count seen in Samples 1-4 compares to Samples 5-8, which did not receive betaine at mixing. Later addition of betaine had no effect on initial count (Samples 2 and 5). Plate counts were redetermined four months later for these samples, and the results are set forth in Table 8.

TABLE 8

| Sample | | Initial Count (cfu's/g) | 4-Month Count (cfu's/g) |
|---|---|---|---|
| With Betaine | 1 | $3.3 \times 10^9$ | $1.9 \times 10^9$ |
| | 2 | $2.5 \times 10^9$ | $1.8 \times 10^9$ |
| | 3 | $2.5 \times 10^9$ | $1.8 \times 10^9$ |
| | 4 | $2.5 \times 10^9$ | $1.8 \times 10^9$ |
| Without Betaine | 5 | $2.1 \times 10^9$ | $1.6 \times 10^9$ |
| | 6 | $2.2 \times 10^9$ | $1.5 \times 10^9$ |
| | 7 | $2.2 \times 10^9$ | $1.4 \times 10^9$ |
| | 8 | $2.6 \times 10^9$ | $1.7 \times 10^9$ |

The results are very similar to the initial plating. Betaine treatments show a slight but consistent increase in cfu's/g.

It will be understood that the foregoing description is of preferred exemplary embodiments of the invention, and that the invention is not limited to the specific forms shown. For example, the slow-drying process of the invention is effective on a variety of bacterial species to provide viable bacteria counts in excess of $10^9$ cells per gram. This and other modifications may be made without departing from the scope of the invention as expressed in the appended claims.

We claim:

1. A process for making a composition containing dormant dried microorganisms, comprising:
   culturing a species of microorganism capable of surviving in a desiccated state selected from *B. japonicum*, *R.*

*meliloti, R. leguminosarum* biovar trifolii, viceae and phaseoli, Bradyrhizobium species for peanut, and *B. lupini* in a growth medium to form a culture;

mixing the culture containing the microorganisms and growth medium with an inert powdered clay carrier; and then incubating the culture-carrier mixture for at least about one day under conditions effective to maintain a substantially constant moisture level in said mixture and to increase the microorganism count in said mixture; and then drying the resulting mixture for at least about one day so that the moisture level in said microorganism is gradually reduced to less than about 15 wt. % on a wet basis to form said composition.

2. The process of claim 1, wherein the weight ratio of culture to carrier in the mixing step is in the range of from 1:2 to 1:4.

3. The process of claim 1, further comprising the step of adding a nutrient to said mixture to enhance growth of said microorganisms during incubation.

4. The process of claim 1, wherein the incubation step is conducted at a temperature in the range of 20° to 30° C. at ambient humidity such that the mixture maintains a moisture level in the range of about 25 to 33 wt. % on a wet weight basis, and the drying step is conducted at a temperature in the range of 20° to 30° C. at a relative humidity of about less than 75%.

5. A process for making a composition containing dormant dried microorganisms, comprising:

culturing a species of microorganism selected from *B. japonicum, R. meliloti, R. leguminosarum* biovar trifolii, viceae and phaseoli, Bradyrhizobium species for peanut, and *B. lupini* in a growth medium to form a culture;

mixing the culture containing the microorganisms and growth medium with an amount of an inert powdered clay effective as a carrier; and then incubating the culture-carrier mixture for at least about one day at a temperature in the range of 20° to 30° C. at ambient humidity such that the mixture maintains a moisture level in the range of about 25 to 33 wt. % on a wet weight basis so that the microorganism count in said mixture increases; and then drying the resulting mixture for at least about one day at a temperature in the range of 20° to 30° C. at a relative humidity of about less than 75% so that the moisture level in said microorganism is gradually reduced to less than about 15 wt. % on a wet basis to form said composition.

6. The process of claim 5, wherein the drying step further comprises maintaining the mixture for about 3 to 14 days at a relative humidity in the range of 35 to 60% so that the moisture level in said microorganism is gradually reduced to about 1 to 5 wt. % on a wet basis.

7. The process of claim 5, wherein the weight ratio of culture to carrier in the mixing step is in the range of from 1:2 to 1:4, and the clay carrier consists essentially of a mixture of kaolinite and montmorillonite having a pH in the range of about 5 to 8.

8. The process of claim 5, further comprising milling the dried mixture to form said composition.

9. The process of claim 8, wherein said milling step further comprises forming particles of said composition having sizes in the range of from about 0.1 to 150 microns.

10. The process of claim 9, further comprising coating seeds of a plant species nodulated by said microorganism with said milled composition.

* * * * *